US006924282B2

(12) United States Patent
Anthony et al.

(10) Patent No.: US 6,924,282 B2
(45) Date of Patent: Aug. 2, 2005

(54) SODIUM SALT OF AN HIV INTEGRASE INHIBITOR

(75) Inventors: Neville J. Anthony, Hatfield, PA (US); Wei Xu, North Wales, PA (US); John V. Lepore, Marlboro, NJ (US); Amar J. Mahajan, Piscataway, NJ (US)

(73) Assignee: Merck & Co., Inc., Rahway, NJ (US)

( * ) Notice: Subject to any disclaimer, the term of this patent is extended or adjusted under 35 U.S.C. 154(b) by 41 days.

(21) Appl. No.: 10/218,537

(22) Filed: Aug. 14, 2002

(65) Prior Publication Data

US 2003/0119823 A1 Jun. 26, 2003

Related U.S. Application Data

(60) Provisional application No. 60/313,373, filed on Aug. 17, 2001.

(51) Int. Cl.[7] .................... C07D 417/14; A61K 31/541; A61P 31/18
(52) U.S. Cl. ........................................ 514/222.2; 544/3
(58) Field of Search ............................ 544/3; 514/222.2

(56) References Cited

U.S. PATENT DOCUMENTS

| | | | |
|---|---|---|---|
| 4,996,213 A | 2/1991 | Mendes et al. | |
| 5,294,620 A | 3/1994 | Ratcliffe et al. | |
| 5,945,431 A | 8/1999 | Jin et al. | |
| 6,262,055 B1 | 7/2001 | Young et al. | |
| 6,294,547 B1 | 9/2001 | Oka et al. | |
| 6,306,891 B1 | 10/2001 | Selnick et al. | |
| 6,380,249 B1 | 4/2002 | Young et al. | |
| 2003/0055071 A1 * | 3/2003 | Anthony et al. ......... | 514/264.1 |

FOREIGN PATENT DOCUMENTS

| | | |
|---|---|---|
| WO | WO 96/25399 A1 | 8/1996 |
| WO | WO 98/11073 A1 | 3/1998 |
| WO | WO 98/13350 A1 | 4/1998 |
| WO | WO 99/10347 A1 | 3/1999 |
| WO | WO 99/32450 A1 | 7/1999 |
| WO | WO 01/00578 A1 | 1/2001 |
| WO | WO 02/04443 A2 | 1/2002 |
| WO | WO 02/06246 A1 | 1/2002 |
| WO | WO 02/30930 A2 | 4/2002 |
| WO | WO 03/035076 A1 | 5/2003 |
| WO | WO 03/035077 A1 | 5/2003 |

OTHER PUBLICATIONS

L. Chan et al., "Discovery of 1,6–Naphthyridines as a Novel Class of Potent and Selective Human Cytomegalovirus Inhibitors", J. Med. Chem., vol. 42, No. 16, pp. 3023–3025 (1999).
L.A. Lasky et al., "Delineation of a Region of the Human Immunodeficiency Virus Type 1 gp120 Glycoprotein Critical for Interaction with the CD4 Receptor", Cell, vol. 50, pp. 975–985 (1987).
L. Ratner et al., "Complete Nucleotide Sequence of the AIDS Virus, HTLV–III", Nature, vol. 313, pp. 277–284 (1985).
H. Toh et al., "Close Structural Resemblance Between Putative Polymerase of a Drosophila Transposable Genetic Element 17.6 and pol gene product of Moloney Murine Leukaemia Virus", The EMBO Journal, vol. 4, No. 5, pp. 1267–1272 (1985).
M.D. Power et al., "Nucleotide Sequence of SRV–1, Type D Simian Acquired Immune Deficiency Syndrome Retrovirus", Science, vol. 231, pp. 1567–1572 (1986).
L.H. Pearl et al., "A Structural Model for the Retroviral Proteases", Nature, vol. 329, pp. 351–354 (1987).
Derwent Abstract No. 97–048296/05 (Abstract of JP 08301849–A, Takeda Chem. Ind. Ltd., "New Heterocyclic Carboxamide Derivs.—Useful in Pharmaceuticals as Tachykinin Receptor Inhibitors").
Chemical Abstracts No. 33–2525; (Abstract of Otiai et al., "Synthesis of 2.5 Naphthyridine Derivatives, II", J. Pharm. Soc. Japan, vol. 58, pp. 764–770 (1938)).
CAPLUS Accession No. 2001:923611, Kiyama et al., "Dual Divalent Metal Ion Chelators as HIV Integrase Inhibitors", Abstract of WO 01/95905, Assignee: Shionogi & Co., Ltd. (2001).
Abstract of WO 02/070486 from http://ipdl.wipo.int (Fuji et al., "Nitrogen–Containing Heteroaryl Compounds Having HIV Integrase Inhibitory Activity", Assignee: Shionogi & Co., Ltd.).
Abstract of WO 02/070491 from http://ipdl.wipo.int (Fuji et al., "Nitrogenous Heteroaromatic Ring Derivative Having HIV Integrase Inhibitory Activity", Assignee: Shionogi & Co., Ltd.).

* cited by examiner

Primary Examiner—James O. Wilson
Assistant Examiner—Kahsay Habte
(74) Attorney, Agent, or Firm—Kenneth R. Walton; Valerie J. Camara

(57) ABSTRACT

A sodium salt of Compound A is disclosed, wherein Compound A is of formula:

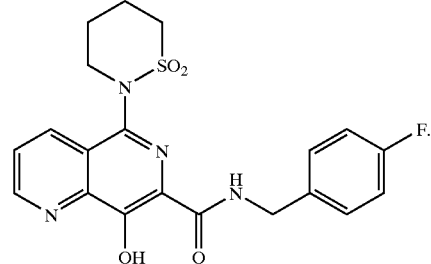

Compound A

Compound A is an HIV integrase inhibitor useful for preventing or treating HIV infection, for delaying the onset of AIDS, and for treating AIDS.

21 Claims, No Drawings

SODIUM SALT OF AN HIV INTEGRASE INHIBITOR

This application claims the benefit of U.S. Provisional Application No. 60/313,373, filed Aug. 17, 2001, the disclosure of which is hereby incorporated by reference in its entirety.

FIELD OF THE INVENTION

The present invention is directed to a pharmaceutically acceptable sodium salt of an HIV integrase inhibitor, Compound A as defined below. The present invention is also directed processes for preparing a sodium salt of Compound A, pharmaceutical compositions containing the salt, and methods for using the salt.

BACKGROUND OF THE INVENTION

The HIV retrovirus is the causative agent for AIDS. The HIV-1 retrovirus primarily uses the CD4 receptor (a 58 kDa transmembrane protein) to gain entry into cells, through high-affinity interactions between the viral envelope glycoprotein (gp 120) and a specific region of the CD4 molecule found in T-lymphocytes and CD4 (+) T-helper cells (Lasky L. A. et al., *Cell* 1987, 50: 975–985). HIV infection is characterized by an asymptomatic period immediately following infection that is devoid of clinical manifestations in the patient. Progressive HIV-induced destruction of the immune system then leads to increased susceptibility to opportunistic infections, which eventually produces a syndrome called ARC (AIDS-related complex) characterized by symptoms such as persistent generalized lymphadenopathy, fever, and weight loss, followed itself by full blown AIDS.

After entry of the retrovirus into a cell, viral RNA is converted into DNA, which is then integrated into the host cell DNA. Integration of viral DNA is an essential step in the viral life cycle. Integration is believed to be mediated by integrase, a 32 kDa enzyme, in three steps: assembly of a stable nucleoprotein complex with viral DNA sequences; cleavage of two nucleotides from the 3' termini of the linear proviral DNA; and covalent joining of the recessed 3' OH termini of the proviral DNA at a staggered cut made at the host target site. The fourth step in the process, repair synthesis of the resultant gap, may be accomplished by cellular enzymes.

The compound 5-(1,1-dioxido-1,2-thiazinan-2-yl)-N-(4-fluorobenzyl)-8-hydroxy-1,6-naphthyridine-7-carboxamide (hereinafter designated herein as "Compound A") is a potent HIV integrase inhibitor. The structure of Compound A is as follows:

Compound A

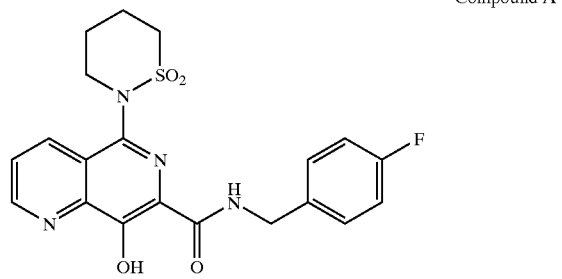

Compound A and structurally related HIV integrase inhibitors are described in WO 02/30930.

SUMMARY OF THE INVENTION

The present invention is directed to a pharmaceutically acceptable alkali metal salt of an HIV integrase inhibitor. More particularly, the present invention includes a sodium salt of Compound A. An embodiment of the present invention is a crystalline sodium salt of Compound A. The sodium salt of Compound A exhibits superior oral absorption and improved pharmacokinetics in animal models compared to crystalline Compound A per se.

The present invention also includes processes for preparing the sodium salt of Compound A and methods of using the Compound A salt for inhibiting HIV integrase, for preventing or treating HIV infection, and for treating or delaying the onset of AIDS.

The foregoing embodiments and other embodiments, aspects and features of the present invention are either further described in or will be apparent from the ensuing description, examples, and appended claims.

DETAILED DESCRIPTION OF THE INVENTION

The present invention provides a pharmaceutically acceptable sodium salt of Compound A, pharmaceutical compositions containing the salt, and methods of making and using the salt. The Compound A sodium salt and pharmaceutical compositions of the present invention are useful for inhibiting HIV integrase, preventing infection by HIV, treating infection by HIV, delaying the onset of AIDS, and treating AIDS, in adults, children or infants. Delaying the onset of AIDS, treating AIDS, or preventing or treating infection by HIV is defined as including, but not limited to, treating a wide range of states of HIV infection: AIDS, ARC, both symptomatic and asymptomatic, and actual or potential exposure to HIV. For example, the sodium salt and pharmaceutical compositions thereof of this invention are useful in treating infection by HIV after suspected past exposure to HIV by, e.g., blood transfusion, exchange of body fluids, bites, accidental needle stick, or exposure to patient blood during surgery. The salts of the invention can also be used in "salvage" therapy; i.e., the sodium salt of Compound A can be used to treat HIV infection, AIDS, or ARC in HIV-positive subjects whose viral load achieved undetectable levels via conventional therapies (e.g., therapies employing known protease inhibitors in combination with one or more known reverse transcriptase inhibitors), and then rebounded due to the emergence of HIV mutants resistant to the known inhibitors.

Compound A is an inhibitor of HIV integrase. Compound A has been tested in an integrase inhibition assay in which strand transfer is catalyzed by recombinant integrase, and has been found to be a potent inhibitor. The strand transfer assay is described in Example 193 of WO 02/30930. Compound A has also been found to be active in an assay for the inhibition of acute HIV infection of T-lymphoid cells conducted in accordance with Vacca et al., *Proc. Natl. Acad. Sci. USA* 1994, 91: 4096–4100.

The crystalline sodium salt of Compound A has exhibited superior oral bioavailability and improved pharmacokinetics (e.g., improved $C_{max}$ and AUC) in rats and dogs relative to amorphous and crystalline Compound A.

An embodiment of the present invention is a crystalline monosodium sodium salt of Compound A. Still another embodiment is the crystalline monosodium salt, characterized by crystallographic d-spacings of 12.6, 5.0, and 4.6 angstroms. Another embodiment of the present invention is a crystalline monosodium salt of Compound A characterized by crystallographic d-spacings of 12.6, 5.0, 4.8, 4.6, 3.9, and 3.5 angstroms. Still another embodiment of the present invention is a crystalline monosodium salt of Compound A characterized by crystallographic d-spacings of 12.6, 5.9, 5.0, 4.9, 4.8, 4.6, 4.5, 4.3, 3.9, 3.7, 3.5, 3.2, 3.1, and 2.9 angstroms. Yet another embodiment of the present invention is a crystalline monosodium salt of Compound A characterized by crystallographic d-spacings of 12.63, 5.94, 5.05, 4.94, 4.81, 4.61, 4.54, 4.34, 3.88, 3.73, 3.49, 3.45, 3.22, 3.15, 3.12, and 2.86 angstroms In an aspect of each of the four preceding embodiments, the Na crystalline salt of Compound A is further characterized by a differential scanning calorimetry curve, at a heating rate of 10° C./min in an open cup under flowing nitrogen, exhibiting an endotherm with a peak temperature of about 348° C. and an associated heat of fusion of about 45 J/gm followed by an exotherm with a peak temperature of about 352° C. and an associated heat of fusion of about 45 J/gm.

The crystallographic d-spacings set forth in the foregoing embodiments can be determined from the XRPD pattern of the crystalline Compound A monosodium salt.

The present invention includes pharmaceutical compositions comprising a sodium salt of Compound A as originally defined above or as set forth in any of the foregoing embodiments or aspects and a pharmaceutically acceptable carrier.

The present invention also includes pharmaceutical compositions which comprise the product made by combining a sodium salt of Compound A as originally defined above or as set forth in any of the foregoing embodiments or aspects and a pharmaceutically acceptable carrier.

Other embodiments of the present invention include the following:

(a) A method of preventing or treating HIV infection in a subject in need thereof, which comprises administering to the subject a therapeutically effective amount of a sodium salt of Compound A.

(b) A method of delaying the onset of AIDS in a subject in need thereof, which comprises administering to the subject a therapeutically effective amount of a sodium salt of Compound A.

(c) A method of treating AIDS in a subject in need thereof, which comprises administering to the subject a therapeutically effective amount of a sodium salt of Compound A.

(d) A method of inhibiting HIV integrase in a subject in need thereof, which comprises administering to the subject a therapeutically effective amount of a sodium salt of Compound A.

(e) A method of preventing or treating HIV infection in a subject in need thereof, which comprises administering to the subject a pharmaceutical composition comprising a therapeutically effective amount of a sodium salt of Compound A and a pharmaceutically acceptable carrier.

(f) A method of delaying the onset of AIDS in a subject in need thereof, which comprises administering to the subject a pharmaceutical composition comprising a therapeutically effective amount of a sodium salt of Compound A and a pharmaceutically acceptable carrier.

(g) A method of treating AIDS in a subject in need thereof, which comprises administering to the subject a pharmaceutical composition comprising a therapeutically effective amount of a sodium salt of Compound A and a pharmaceutically acceptable carrier.

(h) A method of inhibiting HIV integrase in a subject in need thereof, which comprises administering to the subject a pharmaceutical composition comprising a therapeutically effective amount of a sodium salt of Compound A and a pharmaceutically acceptable carrier.

(i) The method of (a) or (b) or (c) or (d), wherein the sodium salt of Compound A is administered in combination with a therapeutically effective amount of at least one AIDS treatment agent selected from the group consisting of AIDS antiviral agents, immunomodulators, and anti-infective agents.

(j) The method of (a) or (b) or (c) or (d), wherein the sodium salt of Compound A is administered in combination with a therapeutically effective amount of at least one antiviral agent selected from the group consisting of HIV protease inhibitors, non-nucleoside HIV reverse transcriptase inhibitors and nucleoside HIV reverse transcriptase inhibitors.

Additional embodiments of the invention include the methods set forth in (a)–(j) above, wherein the sodium salt of Compound A employed therein is a Compound A sodium salt as set forth in any one of the embodiments or aspects described above.

The present invention also includes a process for preparing a sodium salt of Compound A, which comprises dissolving Compound A in a solvent and treating the resulting solution with NaOH to form the sodium salt. A suitable solvent for dissolution of Compound A is a ketone such as a di($C_{1-3}$ alkyl) ketone. In one embodiment, the solvent is acetone. The solution of Compound A can be formed by adding Compound A to the solvent and then heating the mixture to effect dissolution.

Treatment with NaOH typically involves addition of an aqueous solution of NaOH to the solution containing Compound A. NaOH can be added to the Compound A solution in any proportion with respect to Compound A which results in the formation of at least some of the desired sodium salt. However, NaOH is typically added in a proportion which, under the treatment conditions employed (e.g., temperature, degree of agitation), will permit conversion of at least a major portion (and more often substantially all to all) of Compound A to the desired salt. Accordingly, NaOH is typically added in an amount of from about 0.9 to about 5 equivalents per equivalent of Compound A, and is more typically added in an amount of from about 1 to about 2 equivalents per equivalent of Compound A. In one embodiment, Compound A is dissolved in a solvent and treated with from about 1.0 to about 1.3 equivalents of NaOH per equivalent of Compound A.

The treatment of the Compound A solution with NaOH can be conducted at any temperature at which Compound A is soluble in the chosen solvent. Typically, the treatment step is conducted at a temperature in the range of from about 10 to about 80° C., and more typically at a temperature in the range of from about 20 to about 80° C.

Following the addition of NaOH, the solution can be aged for a period of time to permit intimate mixing of NaOH and Compound A. As used herein, the term "aging" and variants thereof (e.g., "aged") mean allowing the reactants (i.e., NaOH and Compound A) to stay in contact for a time and under conditions effective for completion of the reaction. The Compound A solution is optionally agitated (e.g., stirred) during NaOH addition and optionally also during any subsequent aging. At the completion of the treatment step, the desired sodium salt can be recovered by filtration, optionally after cooling or concentrating (e.g., by evaporative removal of solvent by the application of heat and/or vacuum) the treated solution.

The present invention also includes a process for preparing a sodium salt of Compound A, which comprises dissolving a monoethanolate of Compound A in a solvent and treating the resulting solution with NaOH to form the sodium salt. A suitable solvent for dissolution of the Compound A monoethanolate is an alcohol such as a $C_{1-3}$ alkyl alcohol, optionally in admixture with water as a co-solvent. In one embodiment, the solvent is methanol or ethanol. In an aspect of this embodiment the solvent is ethanol. In another aspect, the solvent is ethanol with a minor amount of water as co-solvent. The solution of the Compound A monoethanolate can be formed by adding the monoethanolate to the solvent and then heating the mixture to effect dissolution. The treatment of the solution with NaOH can be conducted as described above.

The present invention also includes a process for preparing a sodium salt of Compound A, which comprises dissolving Compound A in an aprotic solvent selected from the group consisting of N-methyl pyrrolidinone (NMP), N,N-dimethylacetamide, N-ethyl pyrrolidinone, and N,N-dimethylformamide, and treating the resulting solution with NaOH to form the sodium salt. Treatment with NaOH can involve mixing an aqueous solution of NaOH with the solution containing Compound A, but in a preferred embodiment, treatment with NaOH comprises mixing a solution of NaOH in ethanol and water with the solution of Compound A. The relative amounts of NaOH and Compound A employed in this process are as described earlier. Aging of the solution and recovery of the Na salt of Compound A can be conducted as described earlier as well. In a preferred embodiment, Compound A is dissolved in NMP and the Compound A solution is treated with an ethanol-water solution of NaOH. The use of the NMP-EtOH system is characterized by improved filterability of the resulting crystalline Na salt, relative to the EtOH-water system described in the preceding paragraph.

Embodiments of the processes for preparing a sodium salt of Compound A include any of the preparative processes described above, wherein the sodium salt is crystalline. In each of these embodiments, the Compound A solution can optionally also be seeded with a crystalline Na salt of Compound A before, during or subsequent to the addition of NaOH to promote crystal formation. An aspect of each of these embodiments is the preparation of a crystalline monosodium salt of Compound A which is characterized by crystallographic d-spacings of 12.6, 5.0, and 4.6 angstroms. Another aspect of each of these embodiments is the preparation of a crystalline monosodium salt of Compound A which is characterized by crystallographic d-spacings of 12.6, 5.0, 4.8, 4.6, 3.9, and 3.5 angstroms. Still another aspect of each of these embodiments is the preparation of a crystalline monosodium salt of Compound A characterized by crystallographic d-spacings of 12.6, 5.9, 5.0, 4.9, 4.8, 4.6, 4.5, 4.3, 3.9, 3.7, 3.5, 3.2, 3.1, and 2.9 angstroms. Yet another aspect of each of these embodiments is the preparation of a crystalline monosodium salt of Compound A which is characterized by crystallographic d-spacings of 12.63, 5.94, 5.05, 4.94, 4.81, 4.61, 4.54, 4.34, 3.88, 3.73, 3.49, 3.45, 3.22, 3.15, 3.12, and 2.86 angstroms. Further aspects of each of these embodiments include the preparation of a crystalline sodium salt as in any of the three preceding aspects, wherein the Na salt is further characterized by a differential scanning calorimetry curve, at a heating rate of 10° C./min in an open cup under flowing nitrogen, exhibiting an endotherm with a peak temperature of about 348° C. and an associated heat of fusion of about 45 J/gm followed by an exotherm with a peak temperature of about 352° C. and an associated heat of fusion of about 45 J/gm.

As noted above, the present invention includes pharmaceutical compositions useful for inhibiting HIV integrase, comprising an effective amount of a sodium salt of Compound A and a pharmaceutically acceptable carrier. Pharmaceutical compositions useful for preventing or treating infection by HIV, for delaying the onset of AIDS, or for treating AIDS, are also encompassed by the present invention, as well as a method of inhibiting HIV integrase, and a method of preventing or treating infection by HIV, or delaying the onset of AIDS, or treating AIDS. An aspect of the present invention is a pharmaceutical composition comprising a therapeutically effective amount of a sodium salt of Compound A in combination with a therapeutically effective amount of an agent useful for treating HIV infection and/or AIDS (alternatively referred to as an HV/AIDS treatment agent) selected from:

(1) an HIV/AIDS antiviral agent,
(2) an anti-infective agent, and
(3) an immunomodulator.

The present invention also includes the use of a sodium salt of Compound A as described above as a medicament for (a) inhibiting HIV integrase, (b) preventing or treating infection by HIV, (c) delaying the onset of AIDS, or (d) treating AIDS. The present invention further includes the use of a sodium salt of Compound A as described above in the preparation of a medicament for (a) inhibiting HIV integrase, (b) preventing or treating infection by HIV, (c) delaying the onset of AIDS, or (d) treating AIDS.

The present invention also includes the use of a sodium salt of Compound A of the present invention as described above in combination with one or more HIV/AIDS treatment agents selected from an HIV/AIDS antiviral agent, an anti-infective agent, and an immunomodulator for use as a medicament for (a) inhibiting HIV integrase, (b) preventing or treating infection by HIV, (c) delaying the onset of AIDS, or (d) treating AIDS, said medicament comprising an effective amount of the sodium salt of Compound A and an effective amount of the one or more treatment agents.

The present invention further includes the use of a sodium salt of Compound A of the present invention as described above in combination with one or more HIV/AIDS treatment agents selected from an HIV/AIDS antiviral agent, an anti-infective agent, and an immunomodulator for the manufacture of a medicament for (a) inhibiting HIV integrase, (b) preventing or treating infection by HIV, (c) delaying the onset of AIDS, or (d) treating AIDS, said medicament comprising an effective amount of the sodium salt of Compound A and an effective amount of the one or more treatment agents.

For the uses described above, a sodium salt of Compound A of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

The term "administration" and variants thereof (e.g., "administering" a compound) in reference to a sodium salt of Compound A mean providing the salt to the individual in need of treatment. When a salt of the invention is provided in combination with one or more other active agents (e.g., AIDS antivirals), "administration" and its variants are each understood to include concurrent and sequential provision of the salt and other agents.

As used herein, the term "composition" is intended to encompass a product comprising the specified ingredients in the specified amounts, as well as any product which results, directly or indirectly, from combination of the specified ingredients in the specified amounts.

The expression "pharmaceutically acceptable" means that the carrier, diluent or excipient must be compatible with the other ingredients of the formulation and not deleterious to the recipient thereof.

The term "subject," (alternatively referred to herein as "patient") as used herein refers to an animal, preferably a mammal, most preferably a human, who has been the object of treatment, observation or experiment.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation of the symptoms of the disease being treated. For the purpose of prevention of a given disease or condition, a therapeutically effective amount can alternatively be referred to as a prophylactic amount of the active compound or agent.

The pharmaceutical compositions of the present invention may be in the form of orally-administrable capsules, suspensions or tablets, or as nasal sprays, sterile injectible preparations, for example, as sterile injectible aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectible solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters of polyethylene glycols, which are solid at ordinary temperatures, but liquefy and/or dissolve in the rectal cavity to release the drug.

A Compound A sodium salt of this invention can be administered orally to humans on an active ingredient basis in a dosage range of 0.01 to 1000 mg/kg body weight per day in a single dose or in divided doses. One preferred dosage range is 0.1 to 200 mg/kg body weight per day orally in a single dose or in divided doses. Another preferred dosage range is 0.5 to 100 mg/kg body weight per day orally in single or divided doses. For oral administration, the compositions are preferably provided in the form of tablets containing 1 to 1000 milligrams of the active ingredient, particularly 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The present invention is also directed to combinations of a sodium salt of Compound A of the present invention with one or more agents useful in the treatment of HIV infection and/or AIDS. For example, a Compound A salt of this invention may be effectively administered, whether at periods of pre-exposure and/or post-exposure, in combination with effective amounts of the HIV/AIDS antivirals, imunomodulators, antiinfectives, or vaccines, such as those in Table 1 as follows:

TABLE 1

HIV/AIDS ANTIVIRALS, IMUNOMODULATORS, ANTIINFECTIVES, AND OTHER TREATMENTS

| Drug Name | Manufacturer (Tradename and/or Location) | Indication |
|---|---|---|
| ANTIVIRALS | | |
| Amprenavir 141 W94 GW 141 | Glaxo Wellcome (AGENERASE ®) | HIV infection, AIDS, ARC (protease inhibitor) |
| Abacavir GW 1592 1592U89 | Glaxo Welcome (ZIAGEN ®) | HIV infection, AIDS, ARC (reverse transcriptase inhibitor) |
| Acemannan | Carrington Labs (Irving, TX) | ARC |
| Acyclovir | Burroughs Wellcome | HIV infection, AIDS, ARC, in combination with AZT |

TABLE 1-continued

HIV/AIDS ANTIVIRALS, IMUNOMODULATORS, ANTIINFECTIVES, AND OTHER TREATMENTS

| Drug Name | Manufacturer (Tradename and/or Location) | Indication |
|---|---|---|
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL, HIV positive, AIDS |
| Alpha Interferon | Glaxo Wellcome | Kaposi's sarcoma, HIV, in combination w/Retrovir |
| Ansamycin LM 427 | Adria Laboratories (Dublin, OH) Erbamont (Stamford, CT) | ARC |
| Antibody which neutralizes pH labile alpha aberrant Interferon | Advanced Biotherapy Concepts (Rockville, MD) | AIDS, ARC |
| AR 177 | Aronex Pharm | HIV infection, AIDS, ARC |
| beta-fluoro-ddA | Nat'l Cancer Institute | AIDS-associated diseases |
| BMS-232623 (CGP-73547) | Bristol-Myers Squibb/ Novartis | HIV infection, AIDS, ARC (protease inhibitor) |
| BMS-234475 (CGP-61755) | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus immune globin | MedImmune | CMV retinitis |
| Cytovene Ganciclovir | Syntex | sight threatening CMV peripheral CMV retinitis |
| Delavirdine | Pharmacia-Upjohn (RESCRIPTOR ®) | HIV infection, AIDS, ARC (nonnucleoside reverse transcriptase inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche (HIVID ®) | HIV infection, AIDS, ARC |
| ddI Dideoxyinosine | Bristol-Myers Squibb (VIDEX ®) | HIV infection, AIDS, ARC; combination with AZT/d4T |
| mozenavir (DMP-450) | AVID (Camden, NJ) | HIV infection, AIDS, ARC (protease inhibitor) |
| EL10 | Elan Corp, PLC (Gainesville, GA) | HIV infection |
| Efavirenz (DMP 266) | DuPont (SUSTIVA ®) Merck (STOCRIN ®) | HIV infection, AIDS, ARC (non-nucleoside RT inhibitor) |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck (CRIXIVAN ®) | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome (EPIVIR ®) | HIV infection, AIDS, ARC (reverse transcriptase inhibitor); also with AZT |
| Lobucavir | Bristol-Myers Squibb | CMV infection |
| Nelfinavir | Agouron (VIRACEPT ®) | HIV infection, AIDS, ARC (protease inhibitor) |
| Nevirapine | Boeheringer Ingleheim (VIRAMUNE ®) | HIV infection, AIDS, ARC (non-nucleoside reverse transcriptase inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston TX) | HIV infection, AIDS, ARC |
| Ritonavir (ABT-538) | Abbott (RITONAVIR ®) | HIV infection, AIDS, ARC (protease inhibitor) |
| Saquinavir | Hoffmann-LaRoche (FORTOVASE ®) | HIV infection, AIDS, ARC (protease inhibitor) |
| Stavudine; d4T Didehydrodeoxy- thymidine | Bristol-Myers Squibb (ZERIT ®) | HIV infection, AIDS, ARC |
| Valaciclovir | Glaxo Wellcome | genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-La Roche | HIV infection, AIDS, ARC, with AZT |
| Zidovudine; AZT | Glaxo Wellcome (RETROVIR ®) | HIV infection, AIDS, ARC, Kaposi's sarcoma in combination with other therapies (reverse transcriptase inhibitor) |
| Lopinavir (ABT-378) | Abbott | HIV infection, AIDS, ARC (protease inhibitor) |
| Lopinavir + ritonavir (ABT-378/r); Kaletra | Abbott (KALETRA ®) | HIV infection, AIDS, ARC (protease inhibitor) |
| JE2147/AG1776 | Agouron | HIV infection, AIDS, ARC (protease inhibitor) |
| T-20 | Trimeris | HIV infection, AIDS, ARC (fusion inhibitor) |
| T-1249 | Trimeris | HIV infection, AIDS, ARC (fusion inhibitor) |
| atazanavir (BMS 232632); Zrivada | Bristol-Myers-Squibb (ZRIVADA ®) | HIV infection, AIDS, ARC (protease inhibitor) |
| PRO 542 | Progenics | HIV infection, AIDS, ARC (attachment inhibitor) |
| PRO 140 | Progenics | HIV infection, AIDS, ARC (CCR5 co-receptor inhibitor) |
| TAK-779 | Takeda | HIV infection, AIDS, ARC (injectable CCR5 receptor antagonist) |
| DPC 681 & DPC 684 | DuPont | HIV infection, AIDS, ARC (protease inhibitors) |
| DPC 961 & DPC 083 | DuPont | HIV infection AIDS, ARC (nonnucleoside reverse transcriptase inhibitors) |
| abacavir + lamivudine + zidovudine | GlaxoSmithKline (TRIZIVIR ®) | HIV infection, AIDS, ARC (reverse transcriptase inhibitors) |

TABLE 1-continued

HIV/AIDS ANTIVIRALS, IMUNOMODULATORS, ANTIINFECTIVES, AND OTHER TREATMENTS

| Drug Name | Manufacturer (Tradename and/or Location) | Indication |
|---|---|---|
| tipranavir (PNU-140690) | Boehringer Ingelheim | HIV infection, AIDS, ARC (protease inhibitor) |
| tenofovir | Gilead (VIREAD ®) | HIV infection, AIDS, ARC (nucleotide reverse transcriptase inhibitor) |
| TMC-120 & TMC-125 | Tibotec | HIV infections, AIDS, ARC (non-nucleoside reverse transcriptase inhibitors) |
| TMC-126 | Tibotec | HIV infection, AIDS, ARC (protease inhibitor) |
| IMMUNO-MODULATORS | | |
| AS-101 | Wyeth-Ayerst | AIDS |
| Bropirimine | Pharmacia Upjohn | advanced AIDS |
| Acemannan | Carrington Labs, Inc. (Irving, TX) | AIDS, ARC |
| CL246, 738 | American Cyanamid Lederle Labs | AIDS, Kaposi's sarcoma |
| EL10 | Elan Corp, PLC (Gainesville, GA) | HIV infection |
| FP-21399 | Full limmunoPharm | blocks HIV fusion with CD4 + cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoeschst-Roussel Immunex | AIDS |
| Granulocyte Macrophage Colony Stimulating Factor | Schering-Plough | AIDS, combination w/AZT |
| HIV Core Particle Immunostimulant | Rorer | seropositive HIV |
| IL-2 Interleukin-2 | Cetus | AIDS, in combination w/AZT |
| IL-2 Interleukin-2 | Hoffman-La Roche Immunex | AIDS, ARC, HIV, in combination w/AZT |
| IL-2 Interleukin-2 (aldeslukin) | Chiron | AIDS, increase in CD4 cell counts |
| Immune Globulin ntravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma, AIDS, ARC, in combination w/AZT |
| SK&F106528 Soluble T4 | Smith Kline | HIV infection |
| Thymopentin | Immunobiology Research Institute | HIV infection |
| Tumor Necrosis Factor; TNF | Genentech | ARC, in combination w/gamma Interferon |
| etanercept | Immunex Corp (ENBREL ®) | rheumatoid arthritis |
| infliximab | Centocor (REMICADE ®) | rheumatoid arthritis and Crohn's disease |
| ANTI-INFECTIVES | | |
| Clindamycin with Primaquine | Pharmacia Upjohn | PCP |
| Fluconazole | Pfizer | cryptococcal meningitis, candidiasis |
| Pastille Nystatin Pastille | Squibb Corp. | prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | antibacterial |
| Trimethoprim/sulfa | | antibacterial |
| Piritrexim | Burroughs Wellcome | PCP treatment |
| Pentamidine isethionate for inhalation | Fisons Corporation | PCP prophylaxis |
| Spiramycin | Rhone-Poulenc | cryptosporidia diarrhea |
| Intraconazole-R51211 | Janssen Pharm. | histoplasmosis; cryptococcal meningitis |
| Trimetrexate | Warner-Lambert | PCP |
| OTHER | | |
| Daunorubicin | NeXstar, Sequus Ortho Pharm. Corp. | Karposi's sarcoma |
| Recombinant Human Erythropoietin | | severe anemia assoc. with AZT therapy |
| Recombinant Human Growth Hormone | Serono | AIDS-related wasting, cachexia |
| Leukotriene B4 Receptor Antagonist | — | HIV infection |
| Megestrol Acetate | Bristol-Myers Squibb | treatment of anorexia assoc. w/AIDS |
| Soluble CD4 Protein and Derivatives | — | HIV infection |
| Testosterone | Alza, Smith Kline | AIDS-related wasting |
| Total Enteral Nutrition | Norwich Eaton Pharmaceuticals | diarrhea and malabsorption, related to AIDS |

It will be understood that the scope of combinations of a Compound A salt of this invention with HIV/AIDS antivirals, immunomodulators, anti-infectives or vaccines is not limited to the list in Table 1 above, but includes in principle any combination with any pharmaceutical composition useful for the treatment of HIV infection and/or AIDS. When employed in combination with a salt of the invention, the HIV/AIDS antivirals and other agents are typically employed in their conventional dosage ranges and regimens as reported in the art, including the dosages described in the *Physicians' Desk Reference,* 54th edition, Medical Economics Company, 2000. The dosage ranges for a compound of the invention in these combinations are the same as those set forth above just before Table 1.

One suitable combination is a sodium salt of Compound A of the present invention and a nucleoside inhibitor of HIV reverse transcriptase such as AZT, 3TC, ddC, or ddI. Another suitable combination is a Compound A salt of the present invention and a non-nucleoside inhibitor of HIV reverse transcriptase, such as efavirenz, and optionally a nucleoside inhibitor of HIV reverse transcriptase, such as AZT, 3TC, ddC or ddI.

Still another suitable combination is any one of the combinations in the preceding paragraph, further comprising an HIV protease inhibitor such as indinavir, nelfinavir, ritonavir, saquinavir, amprenavir, or abacavir. An aspect of this combination is the combination wherein the HIV protease is the sulfate salt of indinavir. Another aspect of this combination is the combination in which the protease inhibitor is selected from nelfinavir and ritonavir. Still another aspect of this combination is the combination in which the inhibitor of HIV protease is saquinavir, which is typically administered in a dosage of 600 or 1200 mg tid.

Other suitable combinations include a compound of the present invention with the following (1) efavirenz, optionally with AZT and/or 3TC and/or ddI and/or ddC, and optionally with indinavir; (2) any of AZT and/or ddI and/or ddC and/or 3TC, and optionally with indinavir; (3) d4T and 3TC and/or AZT; (4) AZT and 3TC; and (5) AZT and d4T.

In the above-described combinations, a Compound A sodium salt of the present invention and other active agents may be administered together or separately. In addition, the administration of one agent may be prior to, concurrent with, or subsequent to the administration of other agent(s). These combinations may have unexpected or synergistic effects on limiting the spread and degree of infection of HIV.

Abbreviations used herein include the following:

AIDS=acquired immunodeficiency syndrome
ARC=AIDS related complex
Bn=benzyl
DMF=N,N-dimethylformamide
DSC=differential scanning calorimetry
DIPA=diisopropylamine
EDTA=ethylenediamine tetraacetic acid
EtOH=ethanol
g=gram(s)
h=hour(s)
HIV=human immunodeficiency virus
HPLC=high-performance liquid chromatography
IPAc=isopropyl acetate
Me=methyl
MeCN=acetonitrile
MeOH=methanol
min=minute(s)
Ms=mesyl (methanesulfonyl)
MTBE=methyl t-butyl ether
NMP=N-methyl pyrrolidinone
NMR=nuclear magnetic resonance
TEA=triethylamine
THF=tetrahydrofuran
XRPD=x-ray powder diffraction The following examples serve only to illustrate the invention and its practice. The examples are not to be construed as limitations on the scope or spirit of the invention.

EXAMPLE 1

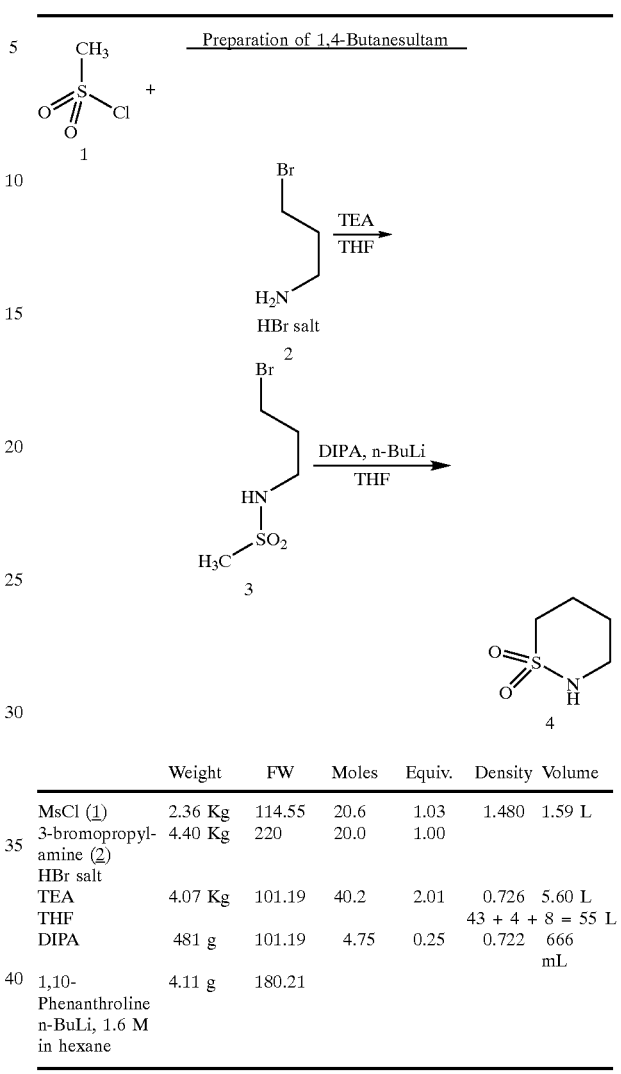

Preparation of 1,4-Butanesultam

| | Weight | FW | Moles | Equiv. | Density | Volume |
|---|---|---|---|---|---|---|
| MsCl (1) | 2.36 Kg | 114.55 | 20.6 | 1.03 | 1.480 | 1.59 L |
| 3-bromopropyl-amine (2) HBr salt | 4.40 Kg | 220 | 20.0 | 1.00 | | |
| TEA | 4.07 Kg | 101.19 | 40.2 | 2.01 | 0.726 | 5.60 L |
| THF | | | | | | 43 + 4 + 8 = 55 L |
| DIPA | 481 g | 101.19 | 4.75 | 0.25 | 0.722 | 666 mL |
| 1,10-Phenanthroline | 4.11 g | 180.21 | | | | |
| n-BuLi, 1.6 M in hexane | | | | | | |

The 3-bromopropylamine-HBr salt (2) and THF (43 L) were placed in a 72 L round-bottomed-flask under $N_2$ and the resulting slurry was cooled to 0° C. Two dropping funnels were fitted to the flask. One was charged with the TEA and the other with a solution of the MsCl (1) and THF (4 L). The contents of the addition funnels were added at roughly the same rate (the TEA was added slightly faster than the MsCl) while maintaining an internal reaction temperature below 10° C. The addition required 2 h. The resulting white suspension was warmed to 23° C. and aged for 1 h. The suspended solids (a mixture of TEA-HBr and TEA-HCl) were removed by filtration through a dry frit. The cake was washed with THF (8 L). The combined filtrate and cake-rinse, a THF solution of 3, was collected in a 100 L round-bottomed-flask under $N_2$. To the solution of 3 was added the 1,10-phenanthroline and the DIPA and the resulting solution was cooled to −30° C. The n-BuLi was added over about 4 h maintaining the internal temperature below −20° C. After 1.25 eq of the n-BuLi was added the reaction mixture became deep brown and the color remained as the addition was completed. The reaction mixture was warmed to 0° C. over 3 h. A small aliquot was removed, and partitioned between saturated $NH_4Cl$ and EtOAc. The EtOAc was evaporated and the residue examined by $^1H$ NMR to confirm consumption of 3 and conversion to 4. To the reaction mixture at 0° C. was added saturated aqueous NH₄Cl (12 L, the first 1 L slowly, a heat kick to 6° C. was observed) and then brine (12 L). The phases were partitioned and the aqueous phase was extracted with EtOAc (20 L). The organic phases were combined, washed with brine (4 L) and then concentrated under vacuum to about 12 L. The solvent was switched to EtOAc (20 L used) maintaining a volume of 12 L. After the solvent switch, a yellow slurry resulted. n-Heptane (20 L) was added with stirring and the slurry was cooled to 5° C. After a 1 h age the solids were collected on a frit and rinsed with cold (5° C.) 3:5 EtOAc/n-heptane. The wet cake was dried for 24 h under a stream of dry N₂ to provide 1.44 Kg (53% from 2) of sultam 4 as a crystalline yellow solid.

$^1$H NMR (CDCl₃, 400 mHz) δ 4.36 (br s, 1H), 3.45 (m, 2H), 3.10 (m, 2H), 2.24 (m, 2H), 1.64 (m, 2H).

EXAMPLE 2

Alternative Preparation of 1,4-Butanesultam
Step 1:

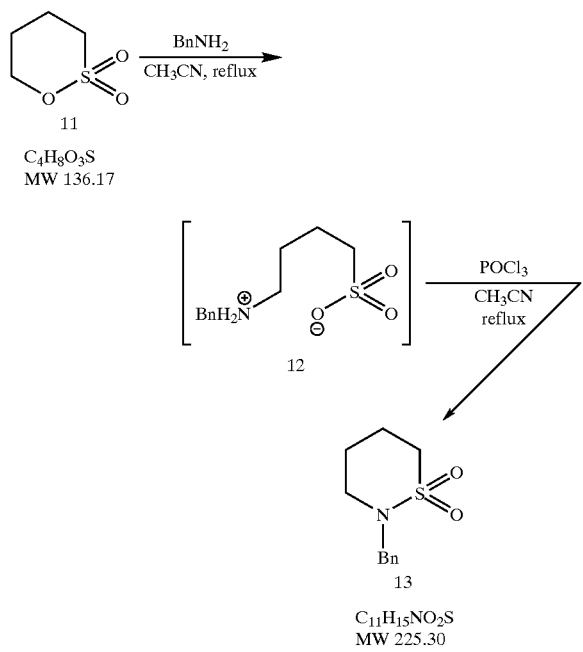

| Materials | MW | Amount | Moles | Equivalent |
|---|---|---|---|---|
| 1,4-Butane sultone | 136.17 | 68.10 g | 0.5000 | 1 |
| Benzylamine | 107.16 | 69.70 g | 0.6500 | 1.3 |
| Acetonitrile | | 625 mL | | |
| Phosphorus oxychloride | 153.33 | 153.33 g | 1.000 | 2 |

A solution of 1,4-butane sultone 11 (68.10 g, 0.5000 moles) and benzylamine (69.70 g, 0.6500 moles) in acetonitrile (625 mL) was refluxed at 82° C. for 24 hours, with the reaction monitored by $^1$H NMR until conversion of 11 to 12 was >98%. While the resulting slurry was cooled to 50° C., phosphorus oxychloride (153.33 g, 1.000 moles) was slowly added via a dropping funnel. After complete addition, the mixture was refluxed at 82° C. for 8 hours, with the reaction monitored by HPLC until conversion was >98%. The reaction mixture was concentrated to remove acetonitrile, and the residue was cooled to 0–5° C. and neutralized with 20% sodium hydroxide to pH=7. The resulting mixture was extracted with IPAc (3×350 mL), and the combined extracts were washed with 10% sodium bicarbonate (2×100 mL) and 25% of brine (100 mL). The resulting clear solution was concentrated and solvent switched to methanol (total volume 1000 mL), which was used in the next step of the reaction. For compound 13: $^1$H NMR (CDCl₃, 400 MHz) δ 7.38–7.32 (m, 5 H), 4.32 (s, 2H), 3.23 (m, 2 H), 3.11 (m, 2 H), 2.22 (m, 2 H), 1.62 (m, 2 H).

Step 2:

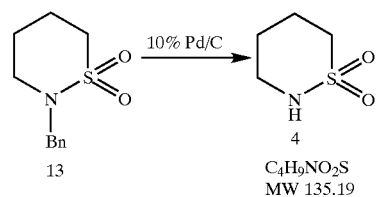

| Materials | MW | Amount | Moles | Equivalent |
|---|---|---|---|---|
| N-Benzyl-1,4-butanesultam | 225.30 | | 0.5000 | 1 |
| 10% Pd/C | | 12.0 g | | 10% wt |
| 1 N HCl (aqueous) | | 80 mL | | |
| Solka Flock | | 20 g | | |

To a solution of N-Benzyl-1,4-butanesultam 13 (0.5000 moles) in methanol (total volume 1000 mL) and 1 N HCl aqueous (80 mL) was added 10% Pd/C (12.0 g). The resulting slurry was submitted to hydrogenation at 40° C., 45 psi for 24 hours, with the reaction monitored by HPLC until conversion of 13 to 4 was >99%. The reaction mixture was cooled to ambient temperature and filtered by passing through a pad of Solka Flock (20 g) and washed with methanol (3×100 mL). The combined filtrates were concentrated to remove the methanol, and a crystalline solid was precipitated out during the concentration. To the slurry solution was added heptane/MTBE (3:2, 100 mL). The resulting mixture was cooled to 0° C., and aged for 0.5 hour. The crystalline solid was filtered off and washed with cold heptane/MTBE (3:2, 50 mL), and dried under vacuum with a nitrogen sweep to give 1,4-butanesultam 4 (49.8 g, 74% overall from 11).

EXAMPLE 3

Preparation of 5-(1,1-dioxido-1,2-thiazinan-2-yl)-N-(4-fluorobenzyl)-8-hydroxy-1,6-naphthyridine-7-carboxamide from methyl 5-bromo-8-hydroxy-1,6-naphthyridine-7-carboxylate Step 1: 5-Bromo-8-hydroxy-1,6-naphthyridine-7-carboxylic Acid Methyl Ester

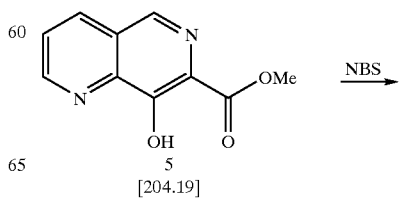

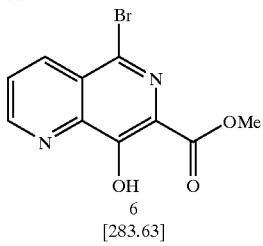

6
[283.63]

N-bromosuccinimide (7.83 g, 44.0 mmol) was added to a solution of 8-hydroxy-1,6-naphthyridine-7-carboxylic acid methyl ester (5, 8.17 g, 40.0 mmol) in chloroform (32 mL) over 20 min maintaining the temperature at 20–50° C. and the mixture was aged for 30 min at 50° C. The mixture became a thick, stirrable slurry and HPLC analysis indicated <2% starting material remaining. The mixture was cooled to 30° C. over 15 min. MeOH (64 mL) was added over 30 min then a 1:1 mixture of MeOH-water (64 mL) was added over 30 min. The mixture was cooled to −40° C. over 30 min and aged at −40° C. for 30 min. The cold mixture was filtered and the solid was washed with 1:1 MeOH:water (100 mL) at 10–20° C. The off white crystalline solid was dried under a stream of nitrogen to provide 10.48 g (93% yield) of 5-bromo-8-hydroxy-1,6-naphthyridine-7-carboxylic acid methyl ester (6).

HPLC retention times: 5=2.2 min, 6=6.0 min, HPLC conditions: 150×4.6 mm ACE 3 C18 column, isocratic elution with 30% MeCN in 0.025% aq $H_3PO_4$ at 1 mL/min, 25° C. with detection at 254 nm;

HPLC retention times: 5=1.8 min, 6=3.1 min, HPLC conditions: 150×4.6 mm ACE 3 C18 column, isocratic elution with 46% MeCN in 0.025% aq $H_3PO_4$ at 1 mL/min, 25° C. with detection at 254 nm.

$^{13}C$ NMR of 6 (CDCl$_3$, 100 MHz): 169.7, 156.3, 154.5, 143.9, 137.1, 132.4, 128.0, 126.1, 124.2, 53.4.

Step 2: 5-Bromo-8-(4-toluenesulfonyloxy)-1,6-naphthyridien-7-carboxylic Acid Methyl Ester

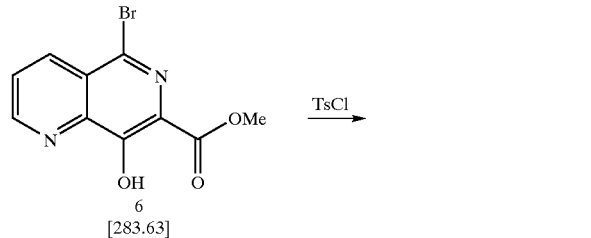

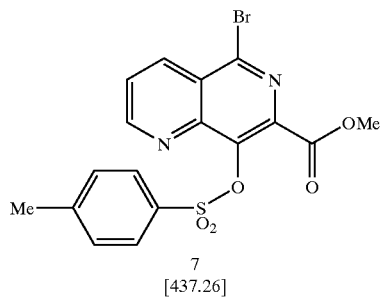

7
[437.26]

Triethylamine (0.759 g, 7.50 mmol) was added to a suspension of 5-bromo-8-hydroxy-1,6-naphthyridine-7-carboxylic acid methyl ester (6, 1.415 g, 5.000 mmol) in chloroform (5 mL) over 5 min maintaining the temperature at 20–50° C. to give a yellow suspension. p-Toluenesulfonyl chloride (1.15 g, 6.00 mmol) was added over 5 min maintaining the temperature at 20–40° C. to give a yellow solution. The mixture was aged at 40° C. for 2 h during which a crystalline solid precipitated out of the mixture and the color faded (HPLC analysis indicated <0.5% starting material remaining). The mixture was cooled to 20° C. over 15 min. MeOH (10 mL) was added over 30 min then a 1:1 mixture of MeOH:water (10 mL) was added over 30 min. The mixture was cooled to −40° C. over 30 min and aged at −40° C. for 30 min. The cold mixture was filtered and the solid was washed with 1:1 MeOH:water (10 mL), MeOH (5 mL), MTBE (10 mL) and hexanes (10 mL) all at 10–20° C. The off-white crystalline solid was dried under a stream of nitrogen to provide 2.112 g (97% yield) of 5-bromo-8-(p-toluenesulfonyloxy)-1,6-naphthyridine-7-carboxylic acid methyl ester (7).

HPLC retention times: 6=3.1 min 7=12.4 min, HPLC conditions: 150×4.6 mm ACE 3 C18 column, isocratic elution with 46% MeCN in 0.025% aq $H_3PO_4$ at 1 mL/min, 25° C. with detection at 254 nm.

$^{13}C$ NMR of 7 (d6-DMSO, 100 MHz): 163.2, 157.0, 146.5, 145.8, 141.9, 141.3, 139.2, 137.2, 132.3, 130.4, 129.0, 127.6, 127.1, 53.3, 21.7.

Step 3: 5-(1,1-Dioxido-1,2-thiazinan-2-yl)-8-(4-toluenesulfonyloxy)-1,6-naphthyridine-7-carboxylic Acid Methyl Ester

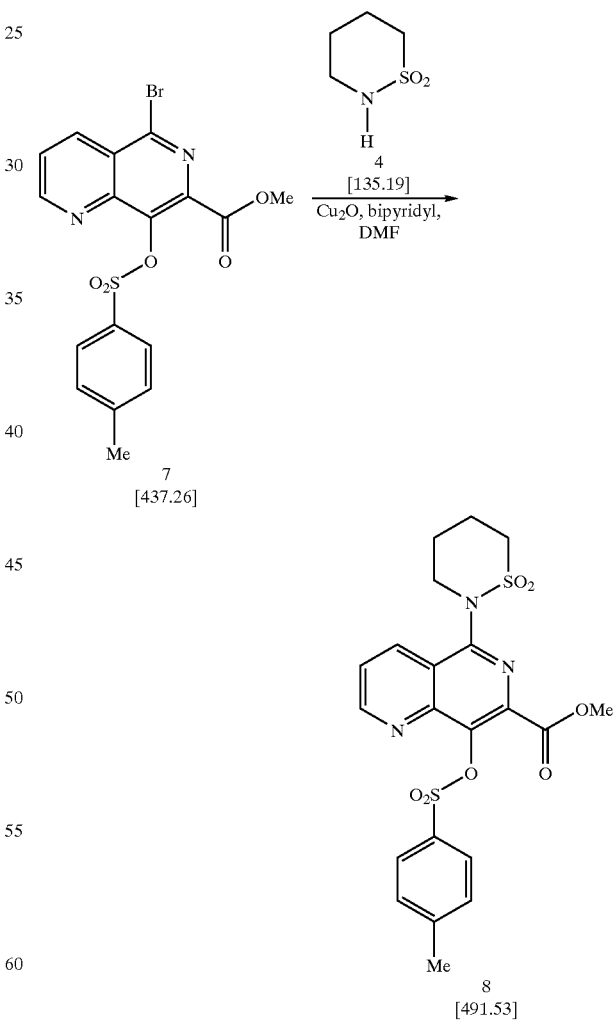

A mixture of 5-bromo-8-(p-toluenesulfonyloxy)-1,6-naphthyridine-7-carboxylic acid methyl ester (7, 2.186 g, 5.000 mmol), 1,4-butane sultam (4, 811 mg, 6.00 mmol), copper (I) oxide (858 mg, 6.00 mmol, <5 micron), 2,2'- bipyridyl (937 mg, 6.00 mmol) and DMF (10 mL) was degassed by stirring under a stream of nitrogen for 1 min and heated to 120° C. for 4 h. The brown suspension became a dark red solution with a small amount of undissolved copper (I) oxide remaining (HPLC analysis indicated <0.5% starting material remaining). The mixture was diluted with chloroform (10 mL), Solkaflok (200 mg) was added and the resulting mixture was filtered through a plug of Solkaflok. The plug was washed with chloroform (10 mL) and the combined filtrates were stirred vigorously with a solution of EDTA disodium salt dihydrate (3.8 g, 10.2 mmol) in water (40 mL) while air was slowly bubbled in for 40 min. The upper aqueous phase became turquoise while the lower organic phase became yellow. The organic phase was washed with a solution of EDTA disodium salt (1.9 g, 5.1 mmol) in water (30 mL) and a solution of sodium bisulfate monohydrate (0.87 g, 6.3 mmol) in water (30 mL). Each of the above three aqueous phases was back extracted sequentially with one portion of chloroform (15 mL). The organic phases were dried over sodium sulfate and filtered. The dried organic extracts were concentrated and solvent switched to a final volume of 15 mL MeOH using a total of 30 mL MeOH for the switch at atmospheric pressure. Product crystallized during the solvent switch. The resulting slurry was cooled to 0° C. over 30 min and aged at 0° C. for 30 min. The slurry was filtered cold and the solid was washed with MeOH (15 mL). The off white solid was dried under a stream of nitrogen to provide 1.910 g (78%) of 5-(N-1,4-butanesultam)-8-(p-toluenesulfonyloxy)-1,6-naphthyridine-7-carboxylic acid methyl ester (8).

HPLC retention times: 7=12.4 min, 8=10.3 min, DMF= 1.3 min, Bipy=1.5 min, HPLC conditions: 150×4.6 mm ACE 3 C18 column, isocratic elution with 46% MeCN in 0.025% aq $H_3PO_4$ at 1 mL/min, 25° C. with detection at 254 nm.

$^{13}$C NMR of 8 (CDCl$_3$, 100 MHz): 164.2, 155.3, 151.9, 146.7, 145.4, 141.2, 137.8, 135.3, 133.6, 129.6, 128.9, 125.4, 124.3, 53.4, 52.9, 48.7, 24.2, 22.0, 21.7.

Step 4: 5-(1,1-Dioxido-1,2-thiazinan-2-yl)-8-hydroxy-1,6-naphthyridine-7-carboxylic Acid Methyl Ester

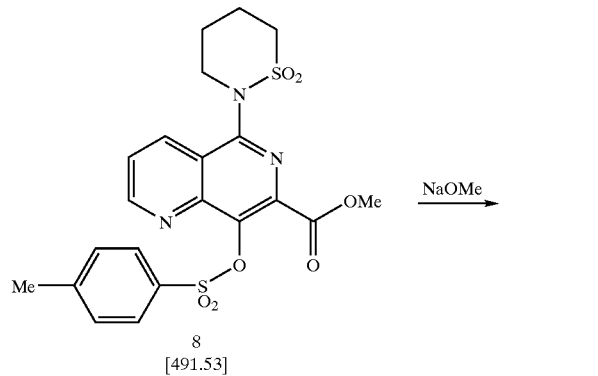

3.250 mmol) was dissolved in DMF (3.25 mL) at 40° C. and transferred to a solution of 0.5M NaOMe in MeOH (16.25 mL, 8.125 mmol) over ca 1–2 min at 20–25° C. The resulting yellow homogenous mixture was heated to 50° C. and aged for 5 min (HPLC analysis indicated <0.5% starting material remaining). Mixture was cooled to 25° C. over 15 min and aged at 25° C. for 15 min during which a yellow crystalline precipitate was deposited. Acetic acid (390 mg, 6.50 mmol) was added over 1 min (yellow color faded) then water (32.5 mL) was added over 15 min at 25° C. The slurry was aged for 30 min 25° C. and filtered. The filter cake was washed with 1:1 MeOH:water (32.5 mL) and then with 1:1 MTBE:hexanes (8 mL). The filter cake was dried under a stream of nitrogen to provide 1.064 g (97%) of 5-(N-1,4-butanesultam)-8-hydroxy-1,6-naphthyridine-7-carboxylic acid methyl ester (9) as an off white crystalline solid.

HPLC retention times: 8=10.3 min, 9=2.9 min, HPLC conditions: 150×4.6 mm ACE 3 C18 column, isocratic elution with 46% MeCN in 0.025% aq $H_3PO_4$ at 1 mL/min, 25° C. with detection at 254 nm.

$^{13}$C NMR of 9 (d6-DMSO, 100 MHz): 167.8, 154.4, 153.5, 143.9, 143.7, 135.2, 125.9, 125.2, 124.4, 53.2, 53.1, 49.1, 24.4, 21.9.

Step 5: 5-(1,1-Dioxido-1,2-thiazinan-2-yl)-N-(4-fluorobenzyl)-8-hydroxy-1,6-naphthyridine-7-carboxamide, Monoethanolate

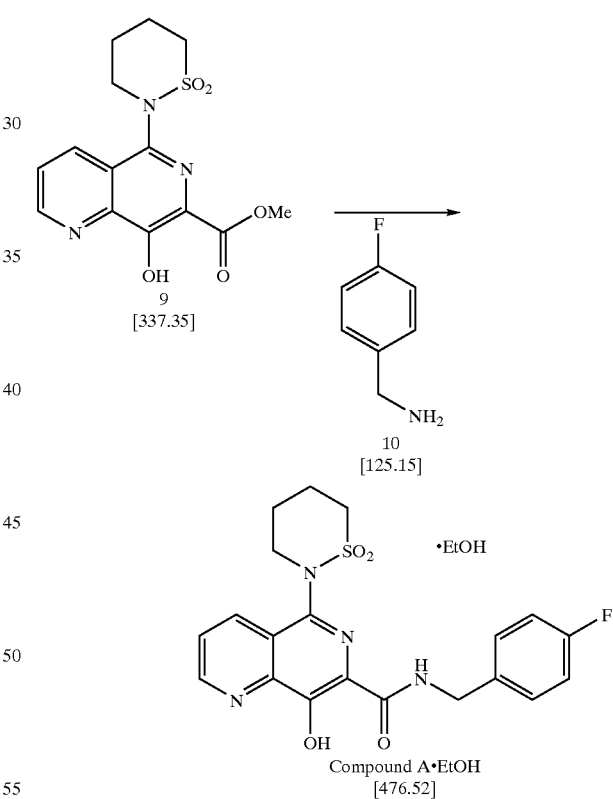

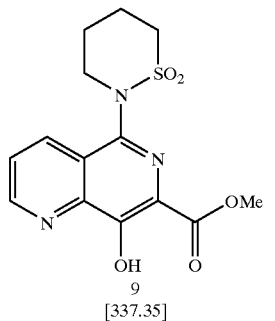

5-(N-1,4-butanesultam)-8-(p-toluenesulfonyloxy)-1,6-naphthyridine-7-carboxylic acid methyl ester (8, 1.597 g, A suspension of 5-(N-1,4-butanesultam)-8-hydroxy-1,6-naphthyridine-7-carboxylic acid methyl ester (9, 1.012 g, 3.00 mmol) and 4-fluorobenzylamine (10, 1.314 g, 10.5 mmol) in EtOH (9.0 mL) was heated to 75–77° C. for 2 h during which the mixture became a yellow homogeneous solution (HPLC analysis indicated <0.5% starting material remaining). Acetic acid (0.630 mg, 10.5 mmol) was added over 1 min (yellow color faded) then water (9.0 mL) was added over 10 min at 75° C. An off white crystalline solid began to precipitate near the end of addition of the water. The slurry was cooled to 0° C. over 30 min then aged for 30 min at 0° C. and filtered. The filter cake was washed with 5% HOAc in 1:1 EtOH:water (5 mL) then with 1:1 EtOH:water (10 mL) and then with EtOH (5 mL). The filter cake was dried under a stream of nitrogen to provide 1.343 g (94%) of the monoethanolate of 5-(N-1,4-butanesultam)-N-(4-fluorobenzyl)-8-hydroxy-1,6-naphthyridine-7-carboxamide (Compound A) as an off white crystalline solid.

HPLC retention times: 9=2.9 min, Compound A=6.7 min, 10=1.4 min, impurity present in 10=4.3 min, HPLC conditions: 150×4.6 mm ACE 3 C18 column, isocratic elution with 46% MeCN in 0.025% aq $H_3PO_4$ at 1 mL/min, 25° C. with detection at 254 nm;

HPLC retention time: 9=10.9 min, HPLC conditions: 150×4.6 mm ACE 3 C18 column, isocratic elution with 24% MeCN in 0.025% aq $H_3PO_4$ at 1 mL/min, 25° C. with detection at 254 nm.

$^1$H NMR (d6-DMSO, 400 MHz): 9.25 (t, J=6.4, 1H), 9.16 (d, J=8.4, 1H), 8.56 (d, J=8.4, 1H), 7.86 (dd, J=8.4, 4.1, 1H), 7.41 (dd, J=8.4, 5.7, 2H), 7.16, t, J=8.8, 2H), 4.60 (d, 6.3, 2H), 4.00–3.70 (m, 2H), 3.65–3.45 (m, 2H), 2.35–2.10 (m, 3H), 1.7 (m, 1H).

Step 6: Sodium salt of 5-(1,1-Dioxido-1,2-thiazinan-2-yl)-N-(4-fluorobenzyl)-8-hydroxy-1,6-naphthyridine-7-carboxamide

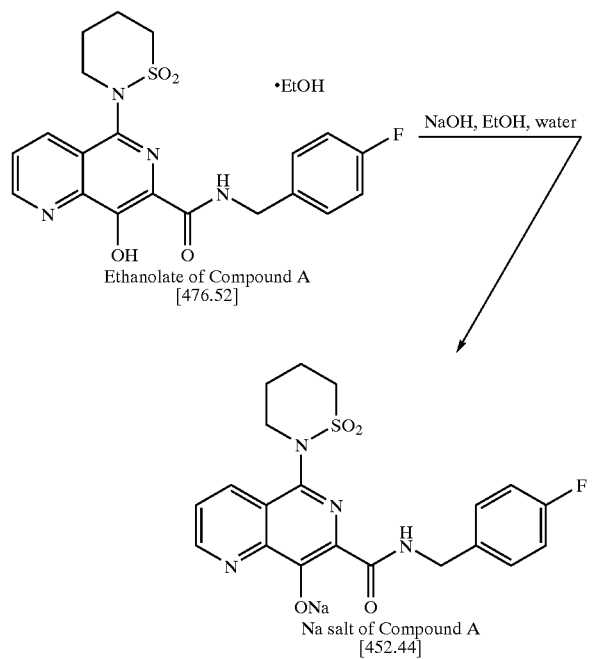

5-(N-1,4-Butanesultam)-N-(4-fluorobenzyl)-8-hydroxy-1,6-naphthyridine-7-carboxamide (Compound A) monoethanolate (1.207 g, 2.533 mmol) was dissolved in a mixture of EtOH (24 mL) and water (11 mL) by heating to 78° C. for 1 h. A solution of 5M aq NaOH (0.608 mL, 3.04 mmol) was added over 15 min at 78° C. A yellow crystalline precipitate was deposited. The mixture was aged at 78° C. for 20 min, then cooled to 20° C. over 30 min and aged for 30 min at 20° C. The slurry was filtered and the filter cake was washed with 2:1 EtOH:water (5 mL) and EtOH (15 mL). The filter cake was dried under a stream of nitrogen to provide 1.088 g (95%) of 5-(N-1,4-butanesultam)-N-(4-fluorobenzyl)-8-hydroxy-1,6-naphthyridine-7-carboxamide sodium salt (Compound A sodium salt) as a yellow crystalline solid.

The Na salt was analyzed by differential scanning calorimetry at a heating rate of 10° C./min in an open cup under flowing nitrogen and was found to have a DSC curve exhibiting an endotherm with a peak temperature of about 348° C. and an associated heat of fusion of about 45 J/gm followed by an exotherm with a peak temperature of about 352° C. and an associated heat of fusion of about 45 J/gm.

The XRPD pattern of the Na salt was generated on a Philips Analytical X-ray powder diffraction instrument with XRG 3100 generator using a continuous scan from 2 to 40 degrees 2 theta over about 126 minutes. The resulting XRPD pattern was analyzed using Philips X'Pert Graphics and Identify software. Copper K-Alpha 1 radiation was used as the source. The experiment was run under ambient conditions. The XRPD pattern was found to have characteristic diffraction peaks corresponding to d-spacings of 12.63, 5.94, 5.05, 4.94, 4.81, 4.61, 4.54, 4.34, 3.88, 3.73, 3.49, 3.45, 3.22, 3.15, 3.12, and 2.86 angstroms.

EXAMPLE 4

Crystallization of Compound A Na Salt from NMP-EtOH Solvent System

A 9 L tank equipped with an agitator was charged with NMP (6.69 kg, 6.67 L) and Compound A (1.00 kg, 2.32 mol) to form a clear yellow solution at room temperature at a concentration of 150 mg/mL. In a separate vessel, 1.1 equivalents of 5M NaOH (0.56 kg, 0.51 L) was diluted to 0.71 M in ethanol (2.45 kg, 3.10 L) at room temperature to form a clear solution. 15% of the phenol in NMP solution (1.17 kg, 1.13 L) was charged to a 16 L jacketed crystallizer equipped with a low blade agitator and heated to 68–70° C. 15% of this NaOH/EtOH solution (0.45 kg, 0.54 L) was combined with the batch in the crystallizer, and the batch aged for 30 to 45 minutes at 68–70° C. Initially, the batch remained a clear yellow solution, but became cloudy after about 5 to 15 minutes, forming a thick yellow slurry, or seed bed consisting of small, evenly distributed needles after about 30 minutes. (Note: As an alternative, the batch may also be seeded with solid seed.)

The remaining Compound A and NaOH solutions were then charged to the batch slurry simultaneously over two hours, maintaining the batch temperature at 65–70° C. The resulting slurry was aged for 1 hour at 68–70° C. Additional EtOH (3.29 kg, 4.13 L) was added as an antisolvent over two hours while still maintaining the batch at 68–70° C., and the thinner yellow slurry aged another hour at 68–70° C. temperature, then cooled to 0–2° C. in about 60 to 90 minutes. The yellow crystalline solid was filtered off on a filter pot at 0–5° C. The filter cake was washed twice with EtOH (8.40 kg, 5.00 L for each wash) at 0–2° C., and the solid vacuum dried for 24–48 hours at 50° C. to provide 1 kg of crystalline Na salt of Compound A.

The sodium salt crystals of Compound A were of a different shape (plates) than those obtained in Example 3 (needles or grains), but they were of the same form as confirmed by XRPD and DSC. The process described in this example exhibits improved filterability and higher productivity than the EtOH-water process exemplified in Example 3.

EXAMPLE 5

Formulation for Oral Administration

As a specific embodiment of an oral composition, 100 mg of the Na salt of Example 3, Step 6 is formulated with sufficient finely divided lactose to provide a total amount of 580 to 590 mg to fill a size O hard gel capsule.

While the foregoing specification teaches the principles of the present invention, with examples provided for the purpose of illustration, the practice of the invention encompasses all of the usual variations, adaptations and/or modifications that come within the scope of the following claims.

What is claimed is:

1. A sodium salt of Compound A, wherein Compound A is of formula:

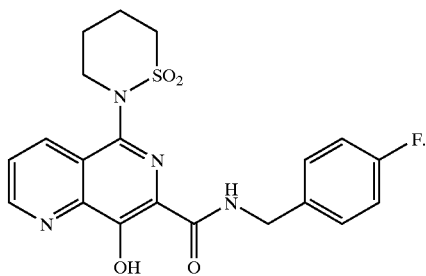

2. The sodium salt according to claim 1, which is a crystalline sodium salt of Compound A.

3. A crystalline monosodium salt of Compound A, characterized by crystallographic d-spacings of 12.6, 5.0, and 4.6 angstroms; wherein Compound A is of formula:

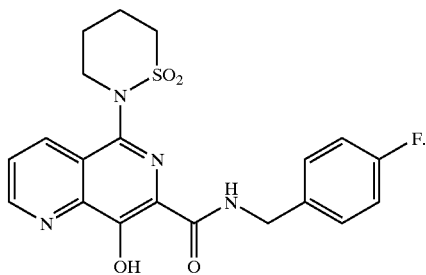

4. The crystalline Na salt of Compound A according to claim 3, which is further characterized by a differential scanning calorimetry curve, at a heating rate of 10° C./min in an open cup under flowing nitrogen, exhibiting an endotherm with a peak temperature of about 348° C. and an associated heat of fusion of about 45 J/gm followed by an exotherm with a peak temperature of about 352° C. and an associated heat of fusion of about 45 J/gm.

5. The crystalline Na salt of Compound A according to claim 3, which is characterized by crystallographic d-spacings of 12.6, 5.0, 4.8, 4.6, 3.9, and 3.5 angstroms.

6. The crystalline Na salt of Compound A according to claim 5, which is further characterized by a differential scanning calorimetry curve, at a heating rate of 10° C./min in an open cup under flowing nitrogen, exhibiting an endotherm with a peak temperature of about 348° C. and an associated heat of fusion of about 45 J/gm followed by an exotherm with a peak temperature of about 352° C. and an associated heat of fusion of about 45 J/gm.

7. The crsytalline Na salt of Compound A according to claim 3, which is characterized by crystallographic d-spacings of 12.6, 5.9, 5.0, 4.9, 4.8, 4.6, 4.5, 4.3, 3.9, 3.7, 3.5, 3.2, 3.1, and 2.9 angstroms.

8. The crystalline Na salt of Compound A according to claim 7, which is further characterized by a differential scanning calorimetry curve, at a heating rate of 10° C./min in an open cup under flowing nitrogen, exhibiting an endotherm with a peak temperature of about 348° C. and an associated heat of fusion of about 45 J/gm followed by an exotherm with a peak temperature of about 352° C. and an associated heat of fusion of about 45 J/gm.

9. A pharmaceutical composition comprising a therapeutically effective amount of a sodium salt of Compound A as recited in claim 1 and a pharmaceutically acceptable carrier.

10. A pharmaceutical composition which comprises the product made by combining a therapeutically effective amount of a sodium salt of Compound A as recited in claim 1 and a pharmaceutically acceptable carrier.

11. A method of treating HIV infection, delaying the onset of AIDS, or treating AIDS in a subject in need thereof, which comprises administering to the subject a therapeutically effective amount of a salt of Compound A as recited in claim 1.

12. A method of inhibiting HIV integrase in a subject in need thereof, which comprises administering to the subject a therapeutically effective amount of a salt of Compound A as recited in claim 1.

13. A method of treating HIV infection, delaying the onset of AIDS, or of treating AIDS in a subject in need thereof, which comprises administering to the subject a pharmaceutical composition according to claim 9.

14. A method of treating HIV infection, delaying the onset of AIDS, or of treating AIDS in a subject in need thereof, which comprises administering to the subject a pharmaceutical composition according to claim 10.

15. A method of inhibiting HIV integrase in a subject in need thereof, which comprises administering to the subject a pharmaceutical composition according to claim 9.

16. A method of inhibiting HIV integrase in a subject in need thereof, which comprises administering to the subject a pharmaceutical composition according to claim 10.

17. A process for preparing a crystalline sodium salt of Compound A, which comprises:

(A) dissolving Compound A in a solvent to form a solution; and (B) treating the solution formed in Step A with NaOH to form the crystalline sodium salt of Compound A.

18. The process according to claim 17, wherein the solvent is acetone.

19. The process according to claim 17, wherein the solvent is NMP and treatment with NaOH comprises mixing the NMP solution of Compound A with an ethanol-water solution of NaOH.

20. A process for preparing a crystalline sodium salt of Compound A, which comprises:

(A) dissolving Compound A monoethanolate in a solvent to form a solution; and (B) treating the solution formed in Step A with NaOH to form the crystalline sodium salt of Compound A.

21. The process according to claim 20, wherein the solvent is ethanol.

* * * * *